(12) United States Patent
Gridnev

(10) Patent No.: US 9,738,647 B2
(45) Date of Patent: Aug. 22, 2017

(54) METHODS FOR THE SYNTHESIS OF POLYCYCLIC GUANIDINE COMPOUNDS

(71) Applicant: Novomer, Inc., Ithaca, NY (US)

(72) Inventor: Alexei Gridnev, Wilmington, DE (US)

(73) Assignee: Saudi Aramco Technologies Company, Dhahran (SA)

( * ) Notice: Subject to any disclaimer, the term of this patent is extended or adjusted under 35 U.S.C. 154(b) by 115 days.

(21) Appl. No.: 14/148,455

(22) Filed: Jan. 6, 2014

(65) Prior Publication Data

US 2014/0194622 A1 Jul. 10, 2014

Related U.S. Application Data

(62) Division of application No. 13/515,634, filed as application No. PCT/US2010/060985 on Dec. 17, 2010, now Pat. No. 8,642,771.

(60) Provisional application No. 61/422,492, filed on Dec. 13, 2010, provisional application No. 61/299,047, filed on Jan. 28, 2010, provisional application No. 61/290,087, filed on Dec. 24, 2009.

(51) Int. Cl.
*C07D 403/02* (2006.01)
*C07D 487/04* (2006.01)

(52) U.S. Cl.
CPC .................. *C07D 487/04* (2013.01)

(58) Field of Classification Search
CPC .................................................... C07D 403/02
USPC ....................................................... 548/303.1
See application file for complete search history.

(56) References Cited

U.S. PATENT DOCUMENTS

| | | | |
|---|---|---|---|
| 2,473,111 A | 6/1949 | Short et al. | |
| 3,873,266 A * | 3/1975 | Hofer et al. | 8/551 |
| 4,157,348 A | 6/1979 | Ono et al. | |
| 4,410,652 A | 10/1983 | Robinson et al. | |
| 4,471,137 A | 9/1984 | Barton et al. | |
| 4,797,487 A | 1/1989 | A'Court | |
| 5,101,041 A | 3/1992 | Troutner et al. | |
| 5,637,739 A | 6/1997 | Jacobsen et al. | |
| 5,659,011 A | 8/1997 | Waldmann | |
| 5,663,393 A | 9/1997 | Jacobsen et al. | |
| 5,665,890 A | 9/1997 | Jacobsen et al. | |
| 5,929,232 A | 7/1999 | Jacobsen et al. | |
| 6,013,675 A | 1/2000 | Durant et al. | |
| 6,130,340 A | 10/2000 | Jacobsen et al. | |
| 6,309,997 B1 | 10/2001 | Fujita et al. | |
| 6,639,087 B2 | 10/2003 | Larrow et al. | |
| 6,844,448 B2 | 1/2005 | Jacobsen et al. | |
| 6,884,750 B2 | 4/2005 | Kim et al. | |
| 6,903,043 B2 | 6/2005 | Kim et al. | |
| 7,145,022 B2 | 12/2006 | Luinstra et al. | |
| 7,244,805 B2 | 7/2007 | Park et al. | |
| 7,544,691 B2 | 6/2009 | Breu et al. | |
| 8,039,618 B2 | 10/2011 | Minch et al. | |
| 8,148,490 B2 | 4/2012 | McCollum et al. | |
| 8,163,867 B2 | 4/2012 | Lee et al. | |
| 8,207,365 B2 | 6/2012 | Zheng et al. | |
| 8,232,267 B2 | 7/2012 | Groves | |
| 8,252,955 B2 | 8/2012 | Gao et al. | |
| 8,288,504 B2 | 10/2012 | Zawacky et al. | |
| 8,334,380 B2 | 12/2012 | Boyd et al. | |
| 8,461,290 B2 | 6/2013 | Carpentier et al. | |
| 8,507,733 B2 | 8/2013 | Ok et al. | |
| 8,598,309 B2 | 12/2013 | Jeong et al. | |
| 8,642,721 B2 | 2/2014 | Ok et al. | |
| 8,642,771 B2 | 2/2014 | Gridnev | |
| 8,791,274 B2 | 7/2014 | Ok et al. | |
| 2009/0281314 A1 | 11/2009 | Boyd et al. | |
| 2010/0256329 A1 | 10/2010 | Nozaki et al. | |
| 2012/0220770 A1 | 8/2012 | Hickenboth et al. | |
| 2014/0249279 A1 | 9/2014 | Williams et al. | |

FOREIGN PATENT DOCUMENTS

| | | |
|---|---|---|
| EP | 2146977 B1 | 11/2012 |
| EP | 2257559 B1 | 10/2014 |
| JP | 53-124220 | 4/1977 |
| JP | 58-035164 | 3/1983 |
| JP | 61-280495 | 12/1986 |
| WO | WO-98/04538 A1 | 2/1998 |
| WO | WO-2005/023781 A1 | 3/2005 |
| WO | WO-2009/137728 A2 | 11/2009 |
| WO | WO-2011/112594 A1 | 9/2011 |

OTHER PUBLICATIONS

Extended European Search Report for EP10840015.1, 6 pages (Jul. 22, 2014).
International Search Report for PCT/US2010/060985, 2 pages (Feb. 28, 2011).
Written Opinion for PCT/US2010/060985, 23 pages (Feb. 28, 2011).

* cited by examiner

*Primary Examiner* — Yong Chu
*Assistant Examiner* — Sonya Wright
(74) *Attorney, Agent, or Firm* — Choate, Hall & Stewart LLP; Charles E. Lyon; Danielle M. Nihan

(57) ABSTRACT

The present invention provides methods for the synthesis of polycyclic guanidine compounds. In certain embodiments, provided methods include the step of contacting a described reagent with a triamine compound to provide a polycyclic guanidine compound.

49 Claims, 1 Drawing Sheet

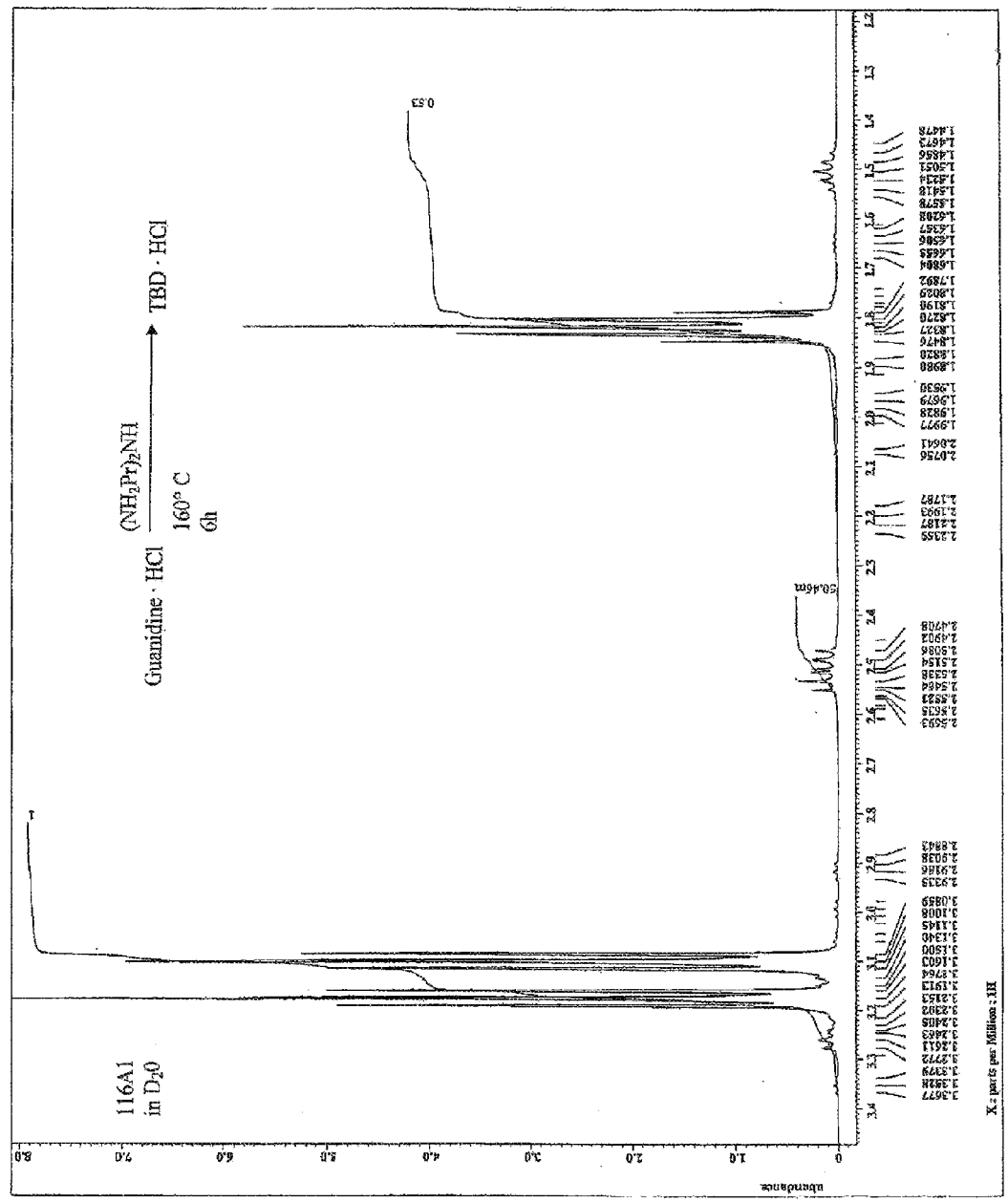

METHODS FOR THE SYNTHESIS OF POLYCYCLIC GUANIDINE COMPOUNDS

CROSS-REFERENCE TO RELATED APPLICATIONS

This application claims priority to U.S. provisional application Ser. No. 61/290,087, filed Dec. 24, 2009, U.S. provisional application Ser. No. 61/299,047, filed Jan. 28, 2010, and U.S. provisional application Ser. No. 61/422,492, filed Dec. 13, 2010 the entirety of each of which is hereby incorporated herein by reference.

BACKGROUND OF THE INVENTION

Highly basic bicyclic and tricyclic guanidine compounds have found applications in the field of organic synthesis and polymer additives. Unfortunately, current methods for synthesizing these compounds either produce noxious byproducts such as hydrogen sulfide or require very harsh conditions.

Bicyclic guanidines such as 1,5,7-triazabicyclo[5.5.0]deco-5-ene (TBD) have been prepared by using triamines in combination with reagents such as $CS_2$ or dialkyl carbonates. The $CS_2$ route is described in U.S. Pat. No. 4,797,487. This route has the benefit of using inexpensive starting materials and providing high yields. However, it also produces large amounts of the poisonous and malodorous compound hydrogen sulfide ($H_2S$) as a reaction byproduct. The generation of $H_2S$ requires additional safety precautions as well as the use of expensive scrubbers to prevent its release into the environment.

A more recent approach is described in US Patent Publication 2009/0281314 and PCT publication WO2009/137728. The route disclosed therein uses cyclic urea as the one carbon source. This is an improvement over the $CS_2$ route since no $H_2S$ is produced; however, the chemistry requires a multi-step process and harsh reaction conditions.

Accordingly, there remains a need for cost effective, inexpensive routes to polycyclic guanidines such as TBD.

SUMMARY OF THE INVENTION

In one aspect, the present invention provides a convenient method for the synthesis of polycyclic guanidine compounds. In certain embodiments, the synthesis includes the step of contacting a described reagent with a triamine compound to provide a polycyclic guanidine compound. As defined herein, the described reagents include guanidine, acyclic guanidines, cyanamide, cyanimides, melamine and melamine derivatives.

In some embodiments, the present invention encompasses methods of synthesizing polycyclic guanidines from guanidine or more generally an acyclic guanidine. In certain embodiments, the methods include the step of contacting an acyclic guanidine with a triamine to provide a polycyclic guanidine compound as shown in Scheme 1 below:

Scheme 1

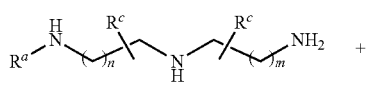
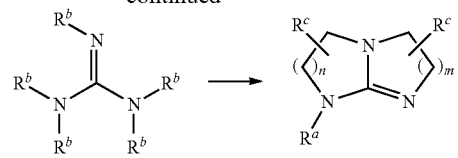

where the variables and R groups are as described herein.

In some embodiments, the present invention encompasses methods of synthesizing polycyclic guanidines from cyanamide or more generally a cyanimide. In certain embodiments, the methods include the step of contacting a cyanimide with a triamine to provide a polycyclic guanidine compound as shown in Scheme 2 below:

Scheme 2

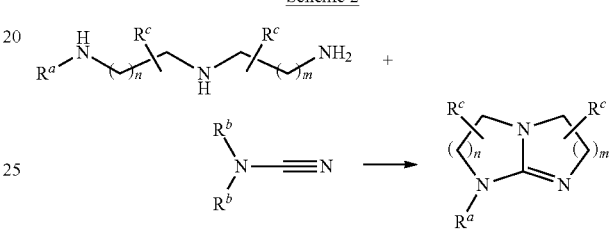

where the variables and R groups are as described herein.

In some embodiment, the present invention encompasses methods of synthesizing polycyclic guanidines from melamine or its derivatives. In certain embodiments, the methods include the step of contacting melamine or a melamine derivative with a triamine to provide a polycyclic guanidine compound as shown in Scheme 3 below:

Scheme 3

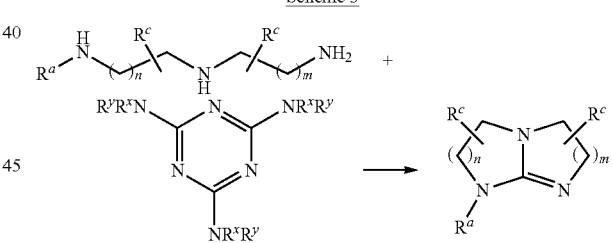

where the variables and R groups are as described herein.

BRIEF DESCRIPTION OF THE DRAWING

FIG. 1 depicts the $^1$H NMR spectrum of a crude TBD product generated using a method of the present invention.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Certain compounds of the present invention may comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of enantiomers or diastereomers are provided.

Furthermore, certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic" or "heteroaliphatic group", as used herein, denotes an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. The term "heteroatom" refers to nitrogen, oxygen, or sulfur, and includes any oxidized form of nitrogen or sulfur, and any quaternized form of a basic nitrogen. The term "nitrogen" also includes a substituted nitrogen. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated monocyclic, bicyclic, or polycyclic ring systems, as described herein, having from 3 to 20 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, bicyclo[2.2.1]heptyl, norbornyl, spiro[4.5]decyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In certain embodiments, the terms "3- to 14-membered carbocycle" and "$C_{3-4}$ carbocycle" refer to a 3- to 8-membered saturated or partially unsaturated monocyclic carbocyclic ring, or a 7- to 14-membered saturated or partially unsaturated polycyclic carbocyclic ring.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms. In some embodiments, alkyl groups contain 1-4 carbon atoms. In certain embodiments, alkyl groups contain 1-3 carbon atoms. In some embodiments, alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms. In some embodiments, alkenyl groups contain 2-4 carbon atoms. In some embodiments, alkenyl groups contain 2-3 carbon atoms. In some embodiments, alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like. In certain embodiments, the terms "6- to 10-membered aryl" and "C$_{6-10}$ aryl" refer to a phenyl or an 8- to 10-membered polycyclic aryl ring. In certain embodiments, the terms "6- to 14-membered aryl" and "C$_{6-14}$ aryl" refer to a phenyl or an 8- to 14-membered polycyclic aryl ring.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 m electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. The term "heteroaralkyl" refers to an alkyl group substituted by a heteroaryl, wherein the alkyl and heteroaryl portions independently are optionally substituted. In certain embodiments, the term "5- to 10-membered heteroaryl" refers to a 5- to 6-membered heteroaryl ring having 1 to 3 heteroatoms independently selected from nitrogen, oxygen, or sulfur, or an 8- to 10-membered bicyclic heteroaryl ring having 1 to 4 heteroatoms independently selected from nitrogen, oxygen, or sulfur. In certain embodiments, the term "5- to 14-membered heteroaryl" refers to a 5- to 6-membered heteroaryl ring having 1 to 3 heteroatoms independently selected from nitrogen, oxygen, or sulfur, or an 8- to 14-membered polycyclic heteroaryl ring having 1 to 4 heteroatoms independently selected from nitrogen, oxygen, or sulfur.

As used herein, the terms "heterocycle", "heterocyclyl", "heterocyclic radical", and "heterocyclic ring" are used interchangeably and refer to a stable 3- to 7-membered monocyclic or 7-14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). In some embodiments, the term "3- to 7-membered heterocyclic" refers to a 3- to 7-membered saturated or partially unsaturated monocyclic heterocyclic ring having 1 to 2 heteroatoms independently selected from nitrogen, oxygen, or sulfur. In some embodiments, the term "3- to 8-membered heterocycle" refers to a 3- to 8-membered saturated or partially unsaturated monocyclic heterocyclic ring having 1 to 2 heteroatoms independently selected from nitrogen, oxygen, or sulfur. In some embodiments, the term "3- to 12-membered heterocyclic" refers to a 3- to 8-membered saturated or partially unsaturated monocyclic heterocyclic ring having 1 to 2 heteroatoms independently selected from nitrogen, oxygen, or sulfur, or a 7- to 12-membered saturated or partially unsaturated polycyclic heterocyclic ring having 1-3 heteroatoms independently selected from nitrogen, oxygen, or sulfur. In some embodiments, the term "3- to 14-membered heterocycle" refers to a 3- to 8-membered saturated or partially unsaturated monocyclic heterocyclic ring having 1 to 2 heteroatoms independently selected from nitrogen, oxygen, or sulfur, or a 7- to 14-membered saturated or partially unsaturated polycyclic heterocyclic ring having 1-3 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a chain or a ring of the depicted molecule. It will be appreciated that this indicates that one or more of the substituents may be attached to the ring or chain at any available position (usually in place of a hydrogen atom of the parent structure). In cases where an atom of a ring or chain so substituted has two substitutable positions, two groups may be present on the same ring atom. Unless otherwise indicated, when more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; $-(CH_2)_{0-4}R°$; $-(CH_2)_{0-4}OR°$; $-O-(CH_2)_{0-4}C(O)OR°$; $-(CH_2)_{0-4}CH(OR°)_2$; $-(CH_2)_{0-4}SR°$; $-(CH_2)_{0-4}Ph$, which may be substituted with $R°$; $-(CH_2)_{0-4}O(CH_2)_{0-1}Ph$ which may be substituted with $R°$; $-CH=CHPh$, which may be substituted with $R°$; $-NO_2$; $-CN$; $-N_3$; $-(CH_2)_{0-4}N(R°)_2$; $-(CH_2)_{0-4}N^+(R°)_3$, $-(CH_2)_{0-4}N(R°)C(O)R°$; $-N(R°)C(S)R°$; $-(CH_2)_{0-4}N(R°)C(O)NR°_2$; $-N(R°)C(S)NR°_2$; $-(CH_2)_{0-4}N(R°)C(O)OR°$; $-N(R°)N(R°)C(O)R°$; $-N(R°)N(R°)C(O)NR°_2$; $-N(R°)N(R°)C(O)OR°$; $-(CH_2)_{0-4}C(O)R°$; $-C(S)R°$; $-(CH_2)_{0-4}C(O)OR°$; $-(CH_2)_{0-4}C(O)N(R°)_2$; $-(CH_2)_{0-4}C(O)SR°$; $-(CH_2)_{0-4}C(O)OSiR°_3$; $-(CH_2)_{0-4}C(O)R°$; $-OC(O)(CH_2)_{0-4}SR-$, $-SC(S)SR°$; $-(CH_2)_{0-4}SC(O)R°$; $-(CH_2)_{0-4}C(O)NR°_2$; $-C(S)NR°_2$; $-C(S)SR°$; $-SC(S)SR°$, $-(CH_2)_{0-4}OC(O)NR°_2$; $-C(O)N(OR°)R°$; $-C(O)C(O)R°$; $-C(O)CH_2C(O)R°$; $-C(NOR°)R°$; $-(CH_2)_{0-4}SSR°$; $-(CH_2)_{0-4}S(O)_2R°$; $-(CH_2)_{0-4}S(O)_2OR°$; $-(CH_2)_{0-4}OS(O)_2R°$; $-S(O)_2NR°_2$; $-(CH_2)_{0-4}S(O)R$; $-N(R°)S(O)_2NR°_2$; $-N(R°)S(O)_2R°$; $-N(OR°)R°$; $-C(NH)NR°_2$; $-P(O)_2R°$; $-P(O)R°_2$; $-OP(O)R°_2$; $-OP(O)(OR°)_2$; $SiR°_3$; $-(C_{1-4}$ straight or branched alkylene)$O-N(R°)_2$; or $-(C_{1-4}$ straight or branched alkylene)$C(O)O-N(R°)_2$, wherein each $R°$ may be substituted as defined below and is independently hydrogen, $C_{1-8}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, $-(CH_2)_{0-2}R^{\bullet}$, -(haloR$^{\bullet}$), $-(CH_2)_{0-2}OH$, $-(CH_2)_{0-2}OR^{\bullet}$, $-(CH_2)_{0-2}CH(OR^{\bullet})_2$; $-O(haloR^{\bullet})$, $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-4}C(O)N(R°)_2$; $-(CH_2)_{0-2}SR^{\bullet}$, $-(CH_2)_{0-2}SH$, $-(CH_2)_{0-2}NH_2$, $(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, $-(C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^{\bullet}$, -(haloR$^{\bullet}$), $-OH$, $-OR^{\bullet}$, $-O(haloR^{\bullet})$, $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^{\dagger}$, $-NR^{\dagger}_2$, $-C(O)R^{\dagger}$, $-C(O)OR^{\dagger}$, $-C(O)C(O)R^{\dagger}$, $-C(O)CH_2C(O)R^{\dagger}$, $-S(O)_2R^{\dagger}$, $-S(O)_2NR^{\dagger}_2$, $-C(S)NR^{\dagger}_2$, $-C(NH)NR^{\dagger}_2$, or $-N(R^{\dagger})S(O)_2R^{\dagger}$; wherein each $R^{\dagger}$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. A substitutable nitrogen may be substituted with three R† substituents to provide a charged ammonium moiety —N⁺(R†)₃, wherein the ammonium moiety is further complexed with a suitable counterion.

Suitable substituents on the aliphatic group of R† are independently halogen, —R●, -(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently C₁₋₄-aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

As used herein, the phrase "described reagent" includes compounds capable of reacting with a triamine to provide a polycyclic guanidine compound. Exemplary such compounds include, but are not limited to, guanidine, acyclic guanidines, cyanamide, cyanimides, melamine and melamine derivatives. The phrase "described reagent" also contemplates salt forms of the above-referenced compounds. By way of non-limiting example, salt forms of guanidine may include guanidine carbonate, guanidine sulfate, guanidine acetate, guanidine nitrate, guanidine p-toluene sulfonate, guanidine hydrochloride, guanidine phosphate and the like.

DETAILED DESCRIPTION OF THE INVENTION

The present invention provides methods for the preparation of polycyclic guanidine compounds. In certain embodiments, provided methods comprise a step of contacting a described reagent with a triamine compound.

In some embodiments, the present invention encompasses methods of synthesizing polycyclic guanidines from guanidine or more generally an acyclic guanidine. In certain embodiments, the methods include the step of contacting an acyclic guanidine with a triamine to provide a polycyclic guanidine compound as shown in Scheme 1 below:

Scheme 1

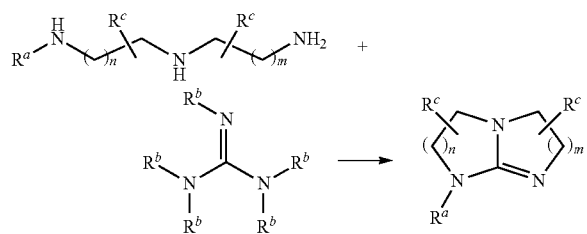

where the variables and R groups are as described herein. In some embodiments each $R^b$ is hydrogen.

In some embodiments, the methods include a step of contacting an acyclic guanidine with a triamine to provide a polycyclic guanidine compound as shown in Scheme 1a below:

Scheme 1a

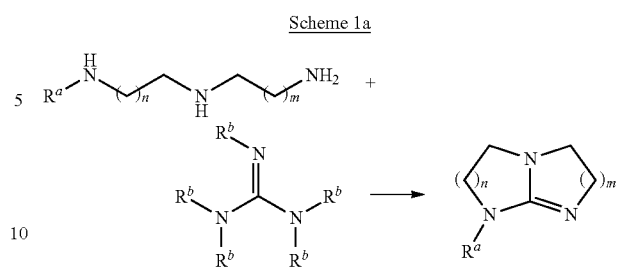

where the variables and other R groups are as described herein. In some embodiments each $R^b$ is hydrogen.

In some embodiments, the methods include a step of contacting an acyclic guanidine with a triamine to provide a polycyclic guanidine compound as shown in Scheme 1b below:

Scheme 1b

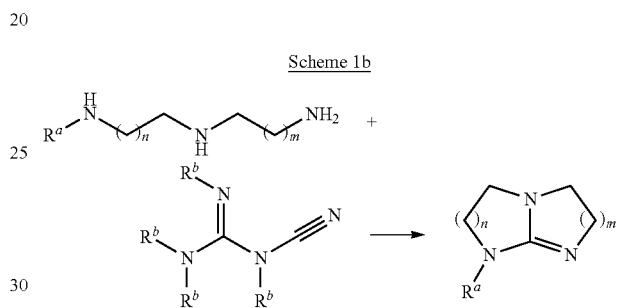

where the variables and other R groups are as described herein. In some embodiments each $R^b$ is hydrogen.

In some embodiments, the present invention encompasses methods of synthesizing polycyclic guanidines from cyanamide or more generally a cyanimide. In certain embodiments, the methods include the step of contacting a cyanimide with a triamine to provide a polycyclic guanidine compound as shown in Scheme 2 below:

Scheme 2

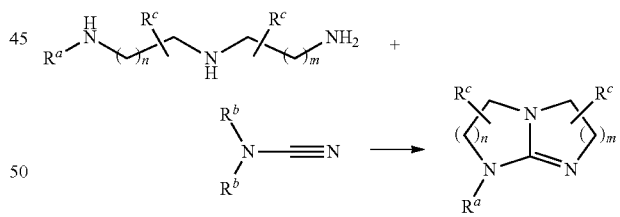

where the variables and R groups are as described herein. In some embodiments each $R^b$ is hydrogen. In some embodiments, each occurrence of $R^b$ is hydrogen or an alkyl group.

In some embodiments, the methods include a step of contacting a cyanimide with a triamine to provide a polycyclic guanidine compound as shown in Scheme 2a below:

Scheme 2a

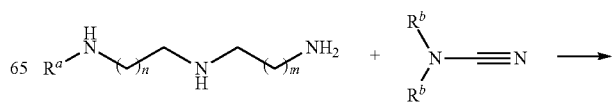

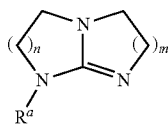

where the variables and other R groups are as described herein. In some embodiments each $R^b$ is hydrogen.

In some embodiments, the present invention encompasses methods of synthesizing polycyclic guanidines from melamine or its derivatives. In certain embodiments, the methods include the step of contacting melamine or a melamine derivative with a triamine to provide a polycyclic guanidine compound as shown in Scheme 3 below:

Scheme 3

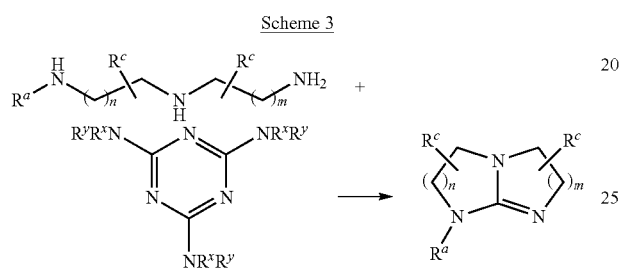

where the variables and other R groups are as described herein. In some embodiments each $R^x$ and $R^y$ is hydrogen. In some embodiments, each occurrence of $R^x$ and $R^y$ is independently hydrogen or an alkyl group.

In some embodiment, the methods include a step of contacting melamine or a melamine derivative with a triamine to provide a polycyclic guanidine compound as shown in Scheme 3a below:

Scheme 3a

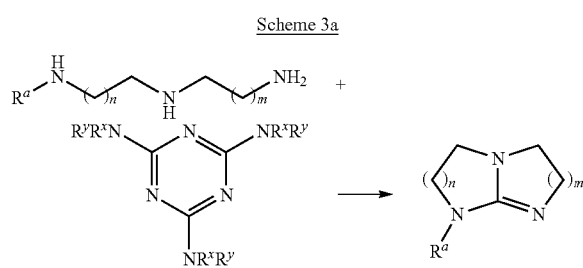

where the variables and other R groups are as described herein. In some embodiments each $R^x$ and $R^y$ is hydrogen.

In certain embodiments, provided methods include contacting a described reagent and a triamine in the presence of a promoter.

In certain embodiments, the promoter is an acid. Suitable acids may include, but are not limited to, mineral acids such as hydrochloric, sulphuric, or phosphoric acid, and organic acids (e.g., sulfonic acids). Suitable sulfonic acids include alkyl or aryl sulfonic acids a large number of which are known to the skilled artisan. Exemplary sulfonic acids include, but are not limited to, methane sulfonic acid, trifluoromethane sulfonic acid, and p-toluene sulfonic acid. In certain embodiments, the acid promoter may include solid supported acids. Solid supported acids can include acid exchange resins (e.g., sulfonic acid resins such as Dowex™ and Amberlyst™ resins) and acids supported on inorganic substrates such as silica or alumina and/or others as are well known in the art.

In certain embodiments the promoter is a base. In certain embodiments, the promoter is a strong base. Suitable bases may include, but are not limited to, one or more metal hydroxides or alkoxides. In certain embodiments, one or more alkoxides of Group I or 11 metals are used. In certain embodiments a sodium alkoxide such as sodium methoxide, sodium ethoxide, sodium isopropoxide, sodium t-butoxide and the like is used. In certain embodiments a lithium alkoxide such as lithium methoxide, lithium ethoxide, lithium isopropoxide, lithium t-butoxide and the like is used. In certain embodiments a potassium alkoxide such as potassium methoxide, potassium ethoxide, potassium isopropoxide, potassium t-butoxide and the like is used.

Reagents

In some embodiments, described reagents suitable for use with a triamine compound in methods of the present invention may include guanidine or more generally an acyclic guanidine of Formula I:

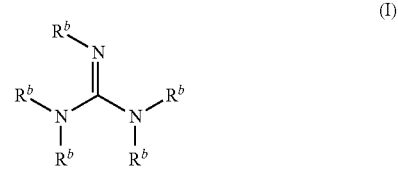

wherein each occurrence of $R^b$ is independently selected from the group consisting of: hydrogen, optionally substituted $C_{1-20}$ aliphatic, optionally substituted aryl and nitrile. In some embodiments, an acyclic guanidine of Formula I is present as a salt or adduct, as described herein.

In certain embodiments, $R^b$ is, at each occurrence, hydrogen and the reagent is guanidine. In certain embodiments, $R^b$ is, at each occurrence, hydrogen or an alkyl group. In certain embodiments, a described acyclic guanidine of the present invention is tetraalkyl guanidine. In certain embodiments, a described acyclic guanidine of the present invention is tetramethyl guanidine.

In certain embodiments, $R^b$ is, at one occurrence, a nitrile (—C≡N). In certain embodiments, $R^b$ is, at one occurrence, nitrile and at all other occurrences, hydrogen or an alkyl group. In certain embodiments, a described acyclic guanidine of Formula I is cyanoguanidine or a derivative thereof.

In some embodiments, described reagents suitable for use with a triamine compound in methods of the present invention may include cyanamide or more generally a cyanimide of Formula II:

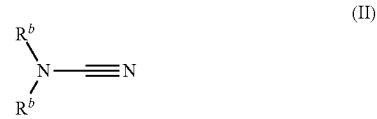

wherein each occurrence of $R^b$ is independently selected from the group consisting of: hydrogen, optionally substituted $C_{1-20}$ aliphatic, and optionally substituted aryl. In some embodiments, a cyanimide of Formula II is present as a salt or adduct.

In certain embodiments, each $R^b$ is hydrogen and the reagent is cyanamide. In certain embodiments, $R^b$ is, at each occurrence, hydrogen or an alkyl group.

In some embodiments, described reagents suitable for use with a triamine compound in methods of the present invention may include melamine or melamine derivatives of Formula III:

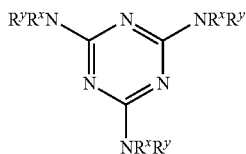
(III)

wherein each occurrence of $R^x$ and $R^y$ is independently selected from the group consisting of hydrogen, optionally substituted $C_{1-20}$ aliphatic, and optionally substituted aryl. In some embodiments, a melamine derivative of Formula III is present as a salt or adduct.

In certain embodiments, $R^x$ and $R^y$ are, at each occurrence, hydrogen and the reagent is melamine. In certain embodiments, $R^x$ and $R^y$ are, at each occurrence, hydrogen or an alkyl group.

In certain embodiments, a salt or adduct of a described reagent may be used in methods of the present invention. In some embodiments, the salt or adduct of a described reagent comprises an acyclic guanidine. In some embodiments, the salt or adduct of a described reagent comprises guanidine. In certain embodiments, methods of the present invention employ a salt of guanidine, such as guanidine carbonate, guanidine sulfate, guanidine acetate, guanidine nitrate, guanidine p-toluene sulfonate, guanidine hydrochloride, guanidine phosphate and the like. In some embodiments, the salt or adduct of a described reagent comprises a cyanimide. In some embodiments, a salt or adduct of a described reagent comprises cyanamide. In some embodiments, the salt or adduct of a described reagent comprises a melamine derivative. In some embodiments, a salt or adduct of a described reagent comprises melamine.

Triamines

In certain embodiments, the triamines employed in the present methods have the Formula IV:

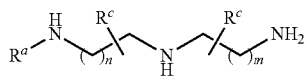
(IV)

wherein:
$R^a$ is selected from the group consisting of hydrogen, optionally substituted aliphatic, optionally substituted heteroaliphatic, optionally substituted aryl, and optionally substituted heteroaryl;
$R^c$ is optionally present, wherein each occurrence of $R^c$ is independently selected from the group consisting of halogen, optionally substituted aliphatic, optionally substituted heteroaliphatic, optionally substituted aryl, and optionally substituted heteroaryl, wherein two or more $R^c$ groups can optionally be taken together with intervening atoms to form one or more optionally substituted rings optionally containing one to three heteroatoms selected from oxygen, nitrogen, or sulfur;
n is an integer from 1 to 4 inclusive; and
m is an integer from 1 to 4 inclusive.

In certain embodiments, a provided method uses a triamine of Formula IV:

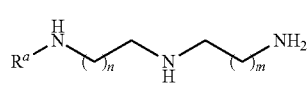
(IVa)

wherein $R^a$, n, and m are as defined above.

In certain embodiments, a triamine is an optionally substituted bis(aminopropyl)amine. In certain embodiments, a triamine is an optionally substituted bis(aminoethyl)amine. In certain embodiments, a triamine is an optionally substituted 2,6-bis(aminomethyl)piperidine. In certain embodiments, a triamine is an optionally substituted 2,6-bis(aminoethyl)piperidine. In certain embodiments, a triamine is an optionally substituted 2,5-bis(aminomethyl)pyrrolidine. In certain embodiments, a triamine is an optionally substituted 2,5-bis(aminoethyl) pyrrolidine. In certain embodiments, a triamine is an optionally substituted N-(2-aminoethyl)-1,3-propanediamine. In certain embodiments, a triamine is an optionally substituted N-(2-aminoethyl)-1,4-butanediamine. In certain embodiments, a triamine is an optionally substituted N-(2-aminopropyl)-1,4-butanediamine.

In certain embodiments, a triamine used in accordance with the present invention is selected from any of those depicted below:

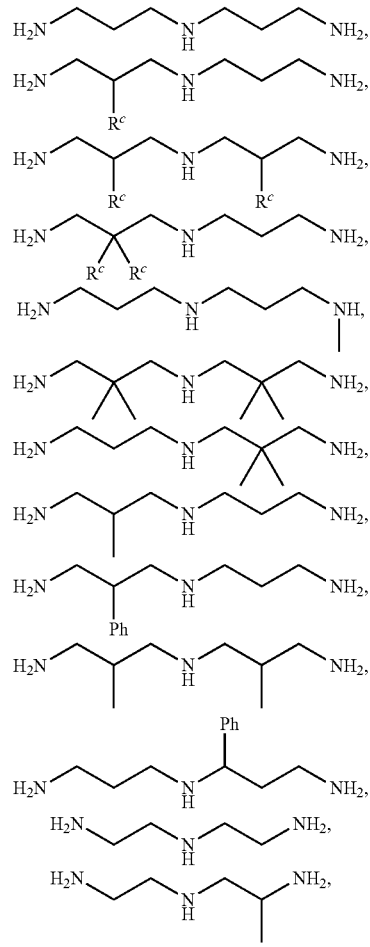

15
-continued

[Structures of various triamines shown]

In certain embodiments, the triamine is of the following structure:

[Structure shown]

In certain embodiments, the triamine is of the following structure:

16

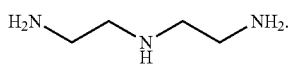

In certain embodiments the triamine is of the following structure:

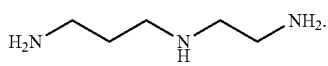

Methods

Methods of the present invention may be performed either in the presence of a solvent, or with a neat mixture of the reagents. Suitable solvents may include common organic solvents such as hydrocarbons, ethers, esters, nitriles, sulfoxides, amides, chlorinated hydrocarbons and/or mixtures of two or more of any one of the above solvents. In certain embodiments, the methods are performed without added solvents.

In some embodiments, methods include the step of heating the reactants. In certain embodiments, the reaction mixture is heated to between about 40° C. and about 300° C. In certain embodiments, the reaction mixture is heated to between about 50° C. and about 250° C. In certain embodiments, the reaction mixture is heated to between about 80° C. and about 200° C. In certain embodiments, the reaction mixture is heated to between about 100° C. and about 180° C. In certain embodiments, the reaction mixture is heated to between about 110° C. and about 180° C. In certain embodiments, the reaction mixture is heated to between about 110° C. and about 170° C. In certain embodiments, the reaction mixture is heated to between about 120 OC and about 170 OC. In certain embodiments, the reaction mixture is heated to between about 130 OC and about 170 OC. In certain embodiments, the reaction mixture is heated to between about 130° C. and about 160° C. In certain embodiments, the reaction mixture is heated to between about 140° C. and about 170° C. In certain embodiments, the reaction mixture is heated to between about 140° C. and about 160° C.

It will be recognized by one skilled in the art that the temperature and length of time a reaction is allowed to proceed can be adjusted to maximize the yield of desired products, minimize side-products and/or most efficiently use laboratory equipment. Based on the teaching and disclosure herein, such modifications and adjustments to the methods presented will be readily apparent to a skilled artisan and the adjustment of these parameters can be a matter of routine experimentation. Such modifications are recognized and specifically encompassed by the scope of the present invention.

In those embodiments of the present invention in which provided methods utilize an acidic promoter, the polycylic guanidine produced by provided methods can be present as an acid salt. In certain embodiments, methods of the present invention further comprise a step of neutralizing such acid salts by treating a product of the reaction with a base. In some embodiments, the step of neutralizing comprises the use of one or more strong bases. In certain embodiments, one or more metal hydroxides or alkoxides are used. In certain embodiments, one or more alkoxides of Group I or II metals are used. In certain embodiments a sodium alkoxide such as sodium methoxide, sodium ethoxide, sodium isopropoxide, sodium t-butoxide and the like is used. In certain embodiments, a solid support and/or polymeric base is used. In certain embodiments, an anion exchange resin may be used to neutralize and/or isolate a product generated using methods of the present invention.

The ratio of reactants can be varied as is typical in the art without departing from the spirit or scope of the present invention. Based on the disclosure and teachings herein, the modification of ratios of reactants (e.g., triamine and a described reagent) can be a matter of routine experimentation for one skilled in the art. In some embodiments, the triamine and the described reagent are present in a molar ratio ranging from about 4:1 to about 1:4. In certain embodiments, they are present in a molar ratio of about 2:1 to about 1:2. In certain embodiments, these reactants are present in approximately equimolar amounts. In certain embodiments, the ratio of the triamine and the described reagent is chosen to approximately correlate with the number of carbon atoms the described reagent can provide for guanidine formation. For example, in embodiments where the described reagent is a guanidine derivative, a ratio of guanidine derivative to triamine of about 1:1 might be employed. Likewise if the described reagent is cyanoguanidine (or a derivative thereof) or melamine (or a melamine derivative), the ratio of described reagent to triamine might be about 1:2 or about 1:3, respectively.

Likewise the amount of promoter can be varied. In certain embodiments, the promoter is present in a ratio of about 1:10 to about 10:1 relative to one or both of the other reactants. In certain embodiments, the described reagent and triamine and an acid promoter are present in about equimolar quantities.

In some embodiments, the present invention encompasses methods for the synthesis of TBD comprising the step of contacting guanidine carbonate with bis(3-aminopropyl) amine in the presence of a sulfonic acid. In certain embodiments, this is done in the absence of added solvents. In certain embodiments, the reactants are heated to between about 80 OC and about 180 OC. In certain embodiments, the reaction is heated for a period less than about 12 h. In certain embodiments, the guanidine carbonate and bis(3-aminopropyl)amine are heated in the presence of methane sulfonic acid. In certain embodiments, the molar ratio between the guanidine carbonate, the triamine, and the sulfonic acid is about 1:1:1.

In some embodiment, the present invention encompasses methods for the synthesis of TBD comprising the step of contacting tetramethylguanidine with bis(3-aminopropyl) amine in the presence of a sulfonic acid. In certain embodiments, this is done in the absence of added solvents. In certain embodiments, the reactants are heated to between about 80° C. and about 180° C. In certain embodiments, the reaction is heated for a period less than about 12 h. In certain embodiments, the tetramethylguanidine and bis(3-aminopropyl)amine are heated in the presence of methane sulfonic acid. In certain embodiments, the molar ratio between the tetramethylguanidine, the triamine, and the sulfonic acid is about 1:1:1.

In some embodiment, the present invention encompasses methods for the synthesis of TBD comprising the step of contacting melamine, or a derivative thereof, with bis(3-aminopropyl)amine in the presence of a sulfonic acid. In certain embodiments, this is done in the absence of added solvents. In certain embodiments, the reactants are heated to between about 80 OC and about 180 OC. In certain embodiments, the reaction is heated for a period less than about 12 h. In certain embodiments, the melamine, or derivative thereof, and bis(3-aminopropyl)amine are heated in the presence of methane sulfonic acid. In certain embodiments, the molar ratio between the melamine, the triamine, and the sulfonic acid is about 1:1:1. In certain embodiments, the molar ratio between the melamine, the triamine, and the sulfonic acid is about 1:2:2. In certain embodiments, the molar ratio between the melamine, the triamine, and the sulfonic acid is about 1:3:3.

EXAMPLES

The following examples are provided as non-limiting demonstrations of certain embodiments of the present invention.

Example 1. Synthesis of TBD Mesylate Using Guanidine Carbonate

A flask was charged with 1.9 g of methane sulfonic acid (0.02 mol) and 3.6 g guanidine carbonate (0.02 mol) and placed into 150 OC bath. After 10 min. 2.6 g of bis(3-aminopropyl)amine (0.02 mol) was added. After 6 h the reaction mixture was cooled and extracted with chloroform. The chloroform solution was evaporated to yield 1.1 g of white solid mass containing TBD mesylate. $^1$H NMR (CDCl$_3$): 8.39 (s, 2H), 3.25 (m, 8H), 2.72 (s, 3H), 1.93 (m, 4H).

Example 2. Alternative Synthesis of TBD Mesylate Using Guanidine Carbonate

A flask was charged with 4.5 g guanidine carbonate (0.025 mol) to which 4.9 g of methane sulfonic acid (0.05 mol) was added. The mixture was heated in a 150° C. oil bath. After 5 min heating, 6.5 g of bis(3-aminopropyl)amine (0.05 mol) was added. After 2 h the reaction mixture was cooled to yield a mass of white solid (13.9 g). Using NMR it was found that about 70% of bis(3-aminopropyl)amine was converted into TBD mesylate.

Example 3. Alternative Synthesis of TBD Mesylate Using Tetramethyl Guanidine 0.98 g of methane sulfonic acid (0.01 mol) was added to a mixture of 1.16 g tetramethyl guanidine (0.01 mol) and 1.3 g of bis(3-aminopropyl)amine (0.01 mol) and placed into 140 OC bath. After 3 h the reaction mixture was chilled and extracted with chloroform. The chloroform solution was evaporated to yield a white solid mass. NMR analysis of the crude product showed 79% conversion of bis(3-aminopropyl)amine into TBD mesylate.

Example 4. Synthesis of TBD Hydrochloride Using Guanidine Hydrochloride 4.8 g guanidine chloride (0.05 mol) and 6.5 g of bis(3-aminopropyl)amine (0.05 mol) were stirred under nitrogen at 160° C. for 6 h. A proton NMR spectrum of the crude product (see FIG. 1) showed 80% conversion of bis(3-aminopropyl)amine into TBD hydrochloride.

Example 5. Synthesis of TBD Carbonate Using Guanidine Carbonate 2.76 g guanidine carbonate (0.012 mol) and 3.25 g of bis(3-aminopropyl)amine (0.025 mol) were stirred under nitrogen at 160 OC for 6 h. A proton NMR spectrum of the crude product showed about 60% conversion of bis(3-aminopropyl)amine into TBD carbonate.

Example 6. Alternative Synthesis of TBD Mesylate Using Cyanoguanidine 0.98 g of methane sulfonic acid (0.01 mol) was added to a mixture of 4.2 g cyanoguanidine (0.05 mol) and 1.3 g of bis(3-aminopropyl)amine (0.01 mol) and placed into 160° C. bath for 6 h. A proton NMR spectrum of the crude product showed 88% conversion of bis(3-aminopropyl)amine into TBD mesylate.

Example 7. Alternative Synthesis of TBD Mesylate Using Cyanamide 1.9 g of methane sulfonic acid (0.02 mol) was added slowly to a mixture of 0.84 g cyanamide (0.02 mol) and 2.6 g of bis(3-aminopropyl) amine (0.02 mol). The reaction mixture was kept for 5 h at 150 OC. A proton NMR spectrum of the crude product showed about 83% conversion of bis(3-aminopropyl) amine into TBD mesylate.

Example 8. Isolation of TBD

TBD mesylate can be purified by solubilization in chloroform. Free TBD can be obtained by adding an equimolar amount of potassium or sodium methylate into a methanol solution of TBD mesylate. TBD may also be isolated from other TBD salts using methods known in the art.

Example 9. Synthesis of 2,3,5,6-tetrahydro-1H-imidazo[1,2-a]imidazole using guanidine hydrochloride

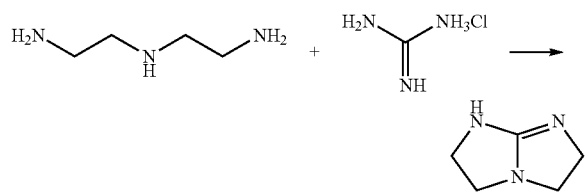

In a scaled vessel, diethylene triamine (0.56 mL, 5.2 mmol) and guanidine hydrochloride (0.50 g, 5.2 mmol) were stirred at 170 OC for 6 h. Afterwards, the melt was allowed to cool to ambient temperature. A white solid was obtained. $^1$H NMR (400 MHz, D$_2$O) δ 3.33 (m, 4H), 3.52 (m, 2H), 3.62 (m, 2H).

Example 10. Synthesis of 1,2,3,5,6,7-hexahydroimidazo[1,2-a]pyrimidine using guanidine hydrochloride

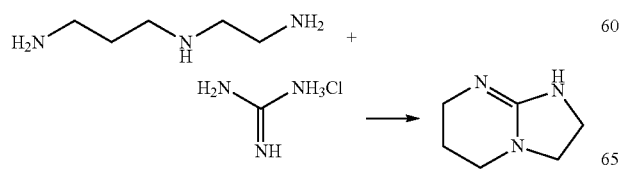

In a sealed vessel, N-(2-aminoethyl)-1,3-propanediamine (0.65 mL, 5.2 mmol) and guanidine hydrochloride (0.50 g, 5.2 mmol) were stirred at 170 OC for 6 h. Afterwards, the melt was allowed to cool to ambient temperature. A white solid was obtained. $^1$H NMR (400 MHz, D$_2$O) δ 1.80 (p, 2H, J=6 Hz), 3.12 (t, 4H, J=5.9 Hz), 3.37 (m, 2H), 3.47 (m, 2H).

Example 11. Synthesis of 2,3,4,6,7,8,9,10-octahydropyrimido[1,2-a][1,3]diazepine using guanidine hydrochloride

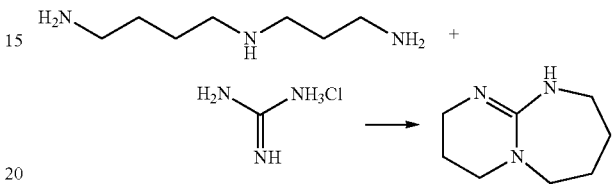

In a sealed vessel, spermidine (0.82 mL, 5.2 mmol) and guanidine hydrochloride (0.50 g, 5.2 mmol) were stirred at 170 OC for 6 h. Afterwards, the melt was allowed to cool to ambient temperature. $^1$H NMR (400 MHz, D$_2$O) δ 1.47 (m, 2H), 1.57 (m, 2H), 1.75 (p, 2H, J=5.7 Hz), 2.97 (t, 2H, J=5.5 Hz), 3.03 (t, 2H, J=5.8 Hz), 3.23 (m, 4H).

EQUIVALENTS

All material cited in this application, including, but not limited to, patents and patent applications, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present disclosure has been particularly shown and described with reference to specific illustrative embodiments, it should be understood that various changes in form and detail may be made without departing from the spirit and scope of the present disclosure. Therefore, all embodiments that come within the scope and spirit of the present disclosure, and equivalents thereto, are intended to be claimed. The claims and descriptions of the present disclosure should not be read as limited to the described order of elements unless otherwise stated.

What is claimed is:

1. A method for the preparation of a polycyclic guanidine compound of Formula V:

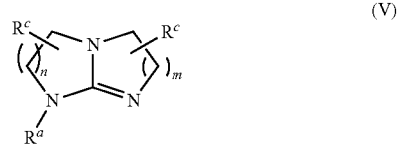

wherein:
R$^a$ is selected from the group consisting of hydrogen, optionally substituted aliphatic, optionally substituted heteroaliphatic, optionally substituted aryl, and optionally substituted heteroaryl;
R$^c$ is optionally present, wherein each occurrence of R$^c$ is independently selected from the group consisting of halogen, optionally substituted aliphatic, optionally substituted heteroaliphatic, optionally substituted awl, and optionally substituted heteroaryl, wherein two or more R$^c$ groups can optionally be taken together with intervening atoms to form one or more optionally substituted rings optionally containing one to three heteroatoms selected from oxygen, nitrogen, or sulfur;
n is an integer from 1 to 4 inclusive; and
m is an integer from 1 to 4 inclusive;
comprising the step of contacting a triamine compound of Formula IV:

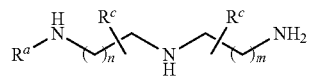
(IV)

with a reagent selected from:
an acyclic guanidine compound of Formula I:

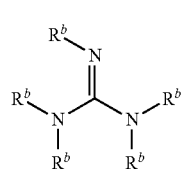
(I)

wherein each occurrence of R$^b$ is independently selected from the group consisting of hydrogen, optionally substituted C$_{1-20}$ aliphatic, optionally substituted aryl and nitrile; or
a cyanimide compound of Formula II:

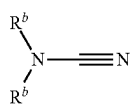
(II)

wherein each occurrence of R$^b$ is independently selected from the group consisting of hydrogen, optionally substituted C$_{1-20}$ aliphatic, optionally substituted aryl; or
melamine or a melamine derivative of Formula III:

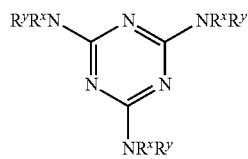
(III)

wherein each occurrence of R$^x$ and R$^y$ is independently selected from the group consisting of hydrogen, optionally substituted C$_{1-20}$ aliphatic, and optionally substituted aryl;

further comprising a step of heating a mixture of the triamine compound of Formula IV and the reagent to a temperature between about 50° C. and about 250° C.

2. The method of claim 1, wherein the reagent is an acyclic guanidine compound of Formula I.

3. The method of claim 2, wherein each occurrence of R$^b$ is hydrogen or optionally substituted C$_{1-20}$ aliphatic, wherein the optionally substituted C$_{1-20}$ aliphatic is an alkyl group.

4. The method of claim 2, wherein the acyclic guanidine compound of Formula I is guanidine.

5. The method of claim 2, wherein the acyclic guanidine compound of Formula I is tetraalkyl guanidine.

6. The method of claim 2, wherein the acyclic guanidine compound of Formula I is tetramethyl guanidine.

7. The method of claim 2, wherein the acyclic guanidine compound of Formula I is in the form of a salt or adduct.

8. The method of claim 2, wherein the acyclic guanidine compound of Formula I is selected from the group consisting of:
guanidine carbonate; guanidine sulfate; guanidine acetate; guanidine nitrate;
guanidine p-toluene sulfonate; guanidine hydrochloride; and guanidine phosphate.

9. The method of claim 2, wherein at least one occurrence of R$^b$ is nitrile.

10. The method of claim 2, wherein the acyclic guanidine compound of Formula I is of Formula Ia:

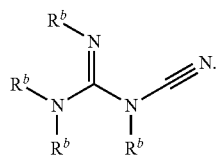
(Ia)

11. The method of claim 2, wherein the acyclic guanidine compound of Formula I is cyanoguanidine.

12. The method of claim 1, wherein the reagent is a cyanimide compound of Formula II.

13. The method of claim 12, wherein each occurrence of R$^b$ is hydrogen.

14. The method of claim 12, wherein each occurrence of R$^b$ is hydrogen or optionally substituted C$_{1-20}$ aliphatic, wherein the optionally substituted C$_{1-20}$ aliphatic is an alkyl group.

15. The method of claim 1, wherein the reagent is melamine or a melamine derivative of Formula III.

16. The method of claim 15, wherein each occurrence of R$^x$ and R$^y$ is independently hydrogen or optionally substituted C$_{1-20}$ aliphatic, wherein the optionally substituted C$_{1-20}$ aliphatic is an alkyl group.

17. The method of claim 15, wherein the reagent is melamine.

18. The method of claim 2, wherein the triamine compound of Formula IV is of Formula IVa:

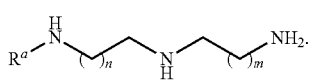
(IVa)

19. The method of claim 1, wherein the triamine compound is an optionally substituted bis(aminopropyl)amine.

20. The method of claim 1, wherein the triamine compound is an optionally substituted bis(aminoethyl)amine.

21. The method of claim 1, wherein the triamine compound is an optionally substituted 2,6-bis(aminomethyl) piperidine.

22. The method of claim 1, wherein the triamine compound is an optionally substituted 2,6-bis(aminoethyl)piperidine.

23. The method of claim 1, wherein the triamine compound is an optionally substituted 2,5-bis(aminomethyl) pyrrolidine.

24. The method of claim 1, wherein the triamine compound is an optionally substituted 2,5-bis(aminoethyl) pyrrolidine.

25. The method of claim 1, wherein the triamine compound is an optionally substituted N-(2-aminoethyl)-1,3-propanediamine.

26. The method of claim 1, wherein the triamine compound is an optionally substituted N-(2-aminoethyl)-1,4-butanediamine.

27. The method of claim 1, wherein the triamine compound is an optionally substituted N-(2-aminopropyl)-1,4-butanediamine.

28. The method of claim 1, wherein the triamine compound is selected from the group consisting of:

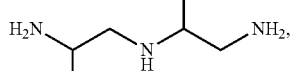
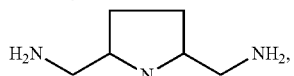
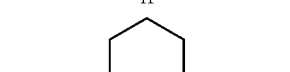
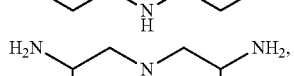
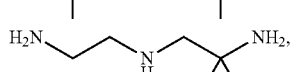
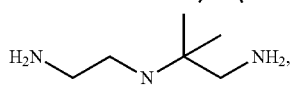
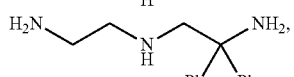
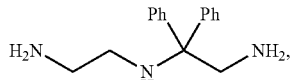
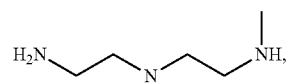
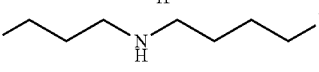
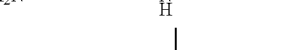
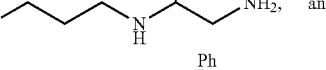
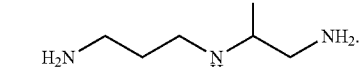

29. The method of claim 1, wherein the triamine compound is of the following structure:

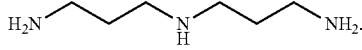

30. The method of claim 1, wherein the triamine compound is of the following structure:

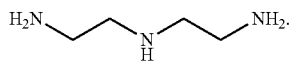

31. The method of claim 1, wherein the triamine compound is of the following structure:

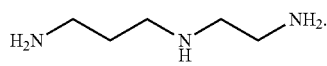

32. The method of claim 1, wherein the triamine compound and the reagent are contacted in the presence of a solvent.

33. The method of claim 1, wherein the triamine compound and the reagent are contacted in the absence of a solvent.

34. The method of claim 1, wherein the mixture is heated to a temperature between about 80° C. and about 200° C.

35. The method of claim 1, wherein the mixture is heated to a temperature between about 100° C. and about 180° C.

36. The method of claim 1, wherein the mixture is heated to a temperature between about 140° C. and about 160° C.

37. The method of claim 1, wherein the triamine compound and the reagent are contacted in the presence of a promoter.

38. The method of claim 37, wherein the promoter is an acid.

39. The method of claim 38, wherein the acid is selected from the group consisting of mineral acids and sulfonic acids.

40. The method of claim 39, wherein the promoter is a sulfonic acid.

41. The method of claim 38, wherein the acid is phosphoric acid.

42. The method of claim 38, wherein the acid is sulfuric acid.

43. The method of claim 40, wherein the sulfonic acid is selected from the group consisting of methane sulfonic acid, ethane sulfonic acid, p-toluene sulfonic acid, and trifluormethyl sulfonic acid.

44. The method of claim 38, further comprising a step of treating a crude product generated from reaction of the reagent and the triamine compound with a strong base.

45. The method of claim 44, wherein the strong base is a metal alkoxide.

46. The method of claim 38, wherein the molar ratio of acid promoter to reagent is from about 10:1 to about 1:10.

47. The method of claim 38, wherein the molar ratio of acid promoter to reagent is about 1:1.

48. The method of claim 1, wherein the molar ratio of triamine compound to reagent is from about 2:1 to about 1:2.

49. The method of claim 48, wherein the molar ratio of triamine compound to reagent is about 1:1.

* * * * *